United States Patent
Clement

(10) Patent No.: US 6,747,038 B2
(45) Date of Patent: Jun. 8, 2004

(54) PHENANTHRIDINE DERIVATIVES AND ANTITUMORAL MEDICAMENTS CONTAINING PHENANTHRIDINE

(76) Inventor: Bernd Clement, Johann-Fleck-Strasse 27, 24106 Kiel (DE)

(*) Notice: Subject to any disclaimer, the term of this patent is extended or adjusted under 35 U.S.C. 154(b) by 0 days.

(21) Appl. No.: 10/415,877

(22) PCT Filed: Oct. 31, 2001

(86) PCT No.: PCT/EP01/12665
§ 371 (c)(1),
(2), (4) Date: May 2, 2003

(87) PCT Pub. No.: WO02/36607
PCT Pub. Date: May 10, 2002

(65) Prior Publication Data
US 2004/0034051 A1 Feb. 19, 2004

(30) Foreign Application Priority Data
Nov. 2, 2000 (DE) .......................... 100 54 337

(51) Int. Cl.$^7$ ............. A61K 31/473; C07D 221/18
(52) U.S. Cl. ................................... 514/284; 546/61
(58) Field of Search ........................ 514/284; 546/61

(56) References Cited

U.S. PATENT DOCUMENTS 6,030,981 A * 2/2000 Clement et al. ............ 514/284

* cited by examiner

Primary Examiner—Charanjit S. Aulakh

(57) ABSTRACT

The invention relates to novel phenanthridine derivatives and to medicaments, which are for use in antitumoral therapy and prophylaxis and which contain these phenanthridine derivatives. It could be shown that up to now specifically substituted phenanthridine derivatives of the prior art neither have a known nor an antitumoral activity that is to be expected.

16 Claims, 1 Drawing Sheet

PHENANTHRIDINE DERIVATIVES AND ANTITUMORAL MEDICAMENTS CONTAINING PHENANTHRIDINE

Figure 1:
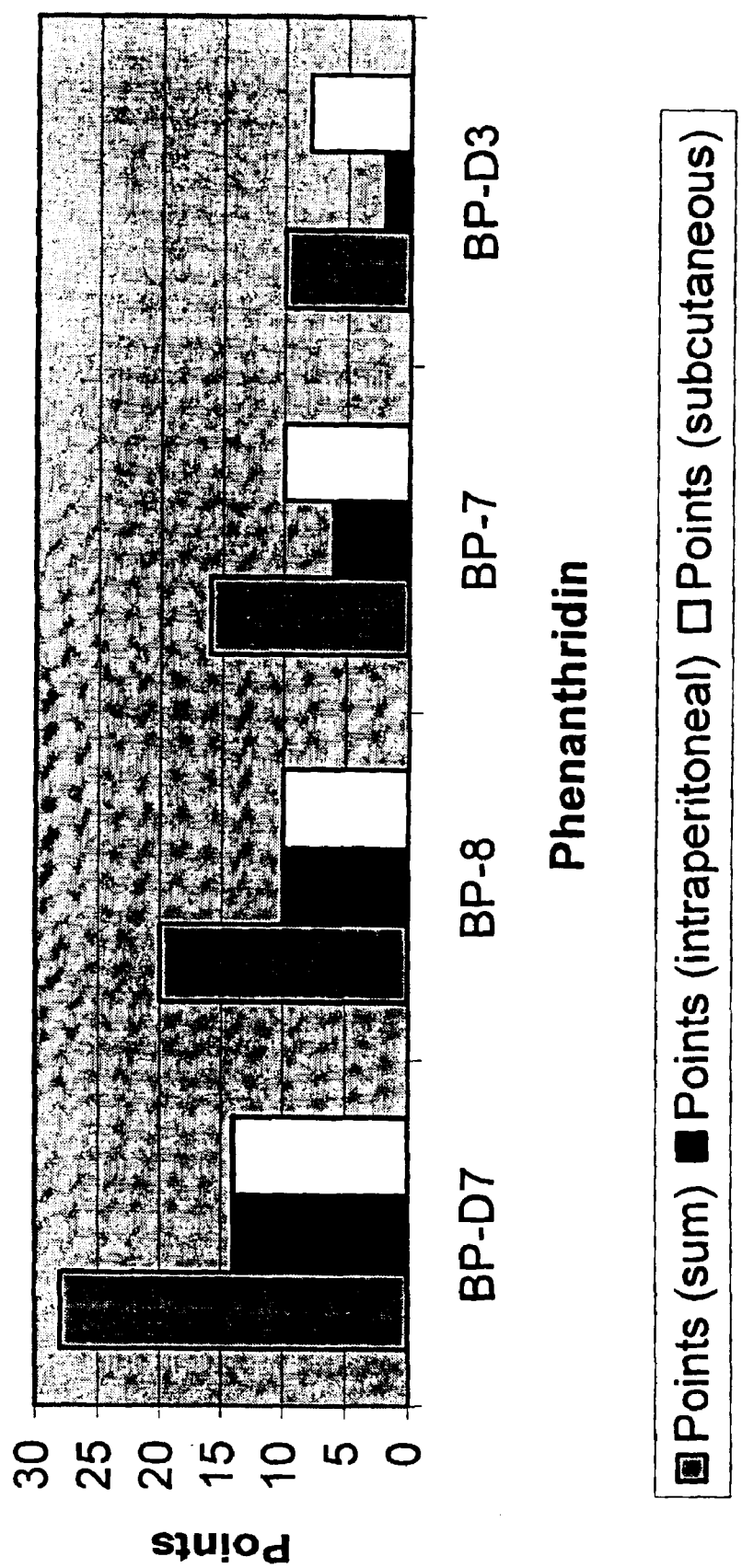

The invention relates to new phenanthridine derivatives as well as pharmaceuticals for a antitumoural therapy and prophylaxis which contain these phenanthridine derivatives. As state of the art WO 97/14683 should be mentioned where phenanthridine derivatives and methods of their preparation are described.

While the synthesis of phenanthridine derivatives is well known for a long time from the technical state and many different synthetic routes exist, the pharmalogical activity has been detected just recently. Thus WO 97/14683 describes for the first time the antitumoral activity of these compounds. However, the antitumoral activity of the described derivatives is limited for a medical application. Starting from this, the objective of this invention is to present new phenanthridine derivatives, similar to the ones described in WO 97/14683, which show a higher antitumoral activity, in comparison to the state of the art.

The objective is achieved with respect to the phenanthridine derivatives by characterising features of claim 1, and with respect to pharmaceuticals by the features of claim 7.

The subclaims demonstrate advantageous further developments. The application of the phenanthridines is mentioned in claims 12 to 16.

In accordance with the invention new phenanthridine derivatives with excellent antitumoural and cytotoxic properties could be delivered. They are defined by the general formular I

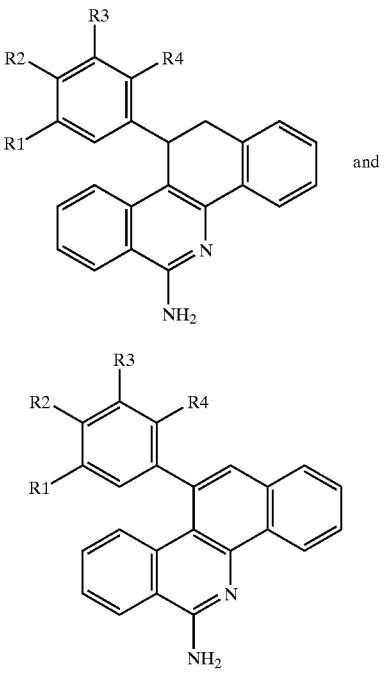

The residues $R_1$ to $R_4$ are selected in a way that three of them are methoxy groups and one is a hydrogen.

Surprisingly it could be demonstrated that phenanthridine derivatives substituted in this way have—from the state of the art—unknown and unexpected antitumour properties. This refers to the subcutaneous as well as to the intraperitoneal application. The known derivatives from WO 97/14683 show less activity in terms of subcutaneous and intraperitoneal usage.

The phenanthridine derivatives presented here show excellent anti-tumour, anti-microbial, anti-fungicidal, anti-viral and anti-inflammatory properties. For the studies of the pharmacological properties, the derivatives have been tested in a "in-vivo-antitumor-Screening" of the National Cancer Institute (NCI) Bethesda, Md., USA.

The derivatives have been tested against a standard panel of twelve human pathogenic tumor cell lines of six different cancer types (non-small cell lung cancer, melanoma, breast cancer, ovarian cancer, colon cancer, CNS cancer).

In the prefered way, the derivatives are present in an ionic from, especially prefered as salts. In accordance with the invention the phenanthridine derivatives exist in acceptable physiologicals salts. Such salts are e.g. salts of inorganic an organic acids, for example hydrochlorides, hydrobromides and sulfates. Especially well suited salts from organic acids are formed with aliphatic mono- and dicarboxylic acids. Examples are acetates, maleates and fumarates.

The following derivatives are prefered according to the highest anti-tumour activity:

A) 6-Amino-11-(3',4',5'-trimethoxyphenyl)benzo[c]phenanthridine perchlorate with the structure presented by formula III,

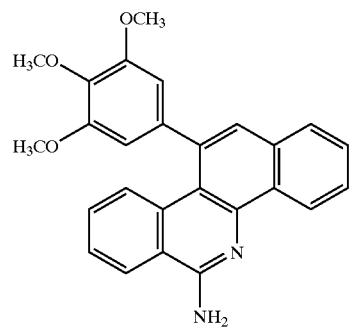

B) 6-Amino-11,12-dihydro- 11-(2',3',4'-trimethoxyphenyl)benzo[c]phenanthridine hydrochloride with the structure presented by formula IV

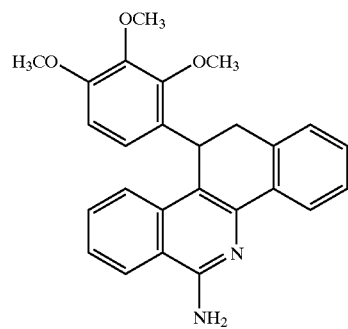

C) 6-Amino- 11,12-dihydro- 11-(3',4',5'-trimethoxyphenyl)benzo[c]phenanthridine hydrochloride with the structure represented by formula V

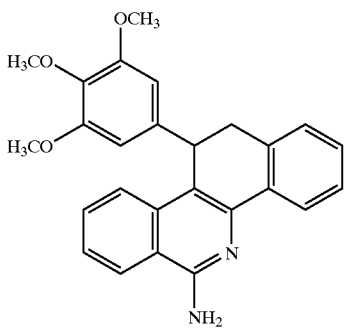

Formula V

The invention also relates therefor to medicines containing phenanthridine derivatives which are described here. The medicine contains, for this purpose, at least one phenanthridine derivative, in the manner described here, together with at least one inert pharmaceutically acceptable carrier or dilution medium. A derivative of the general formula III, IV and/or V is preferred as a phenanthridine derivative. The compound, according to the invention, can be administered orally, topically or parenterally, or in the form of suppositories. The preferred mode of administration is oral administration. This can be administered in the form of the base or as a physiologically acceptable salt. It is generally mixed with a pharmaceutically acceptable carrier or dilution medium, in order to create a medicine. For oral administration the medicine can be made available most usefully in the form of capsules or tablets or possibly even slow-release tablets. They can also be available in the form of dragees or in syrup form. Suitable topic preparations are e.g. salts, lotions, creams, powders and sprays.

In the same way the invention concerns the usage of at least one of the above named phenanthridine derivatives for the preparation of a medicine for an anti-tumour therapy and prophylaxis.

The further examples and figures describe in greater detail the properties of the compounds presented in this invention.

EXAMPLE 1

Synthesis of 6-Amino-11-(3',4',5'-trimethoxyphenyl)benzo[c]phenanthridine Perchlorate To a solution of 4.85 mmol (2.0 g) 6-Amino-11,12-dihydro-11-(3',4',5'-tri-methoxyphenyl)benzo[c]phenanthridine in 120 ml dioxane a solution of 19.4 mmol (4.63 g) DDQ in 100 ml dioxane is added and heated under reflux for 16 h. The cooled reaction mixture is than hydrolysed with 500 ml saturated sodium hydrocarbonate solution and stirred vigorously for 30 minutes. The aqueous phase is than extracted three times with 200 ml ether, the combined organic extracts were washed once with 300 ml saturated sodium hydrocarbonate solution and three times with 250 ml water. Then the organic phase is dried over sodium sulfate if needed and rotated to about 150 ml. For precipitation of the 6-Amino-11,12-dihydro-11-(3',4',5'-trimethoxy-phenyl)benzo[c]phenanthridine perchlorate the organic phase is stirred over night with 10 ml 70% perchloric acid or if needed with 20 ml 70% perchloric acid, ethanol and ether (1/1/1).

The brown precipitation is collected, washed with a small portion of ether and recrystallized in methanol and dried for 24 h in an oil pump vacuum.

Yield: 1.12g (44% of theory), darkbrown needles
melting point: 296° C.

| $C_{26}H_{23}N_2O_7Cl$ (510.93) | Calc.: | C 61.12 | H 4.54 | N 5.48 |
| | | O 21.92 | Cl 6.94 | |
| | Found: | C 61.10 | H 4.55 | N 5.40 |

$^1$H-NMR (DMSO-d$_6$, 300 MHz): δ/ppm (TMS)=3.73 (s, 6H, 2 —OCH$_3$), 3.79 (s, 3H, —OCH$_3$), 6.77 (s, 2H, ArH), 7.65–7.95 (m, 6H, ArH), 8.14 (d, 1H, ArH), 8.67 (d, 2H, ArH), 9.82 (br, s, 2H, —NH$_2$), 12.95 (br, s, 1H, ≡N$^+$—H).

$^{13}$C-NMR (DMSO-d$_6$, 75 MHz): δ/ppm (TMS)=56.1 (2 C, 2 —OCH$_3$), 60.3 (—OCH$_3$), 106.3 (2C), 121.1, 126.1, 127.6, 127.9, 128.1, 128.4, 128.7, 128.9, 133.2(11C, C-1, -2, -3, -4, -7, -8, -9, -10, -12, -2', -6'), 114.9, 118.1, 121.8, 130.4, 132.3, 134.2, 136.6, 137.4, 137.7, 153.5 (2C), 154.6, (12C, C-4a, -4b, -6, -6a, -10a, -10b, -11, -12a, -1', -3', -4', -5').

MS (EI): m/z (%)=410 (M$^+$ of the base, 100), 395 (M$^+$ —CH$_3$, 20), 380 (M$^+$ -2CH$_3$,3), 363 (6), 352 (9), 335 (8), 320 (9), 305 (8), 292 (15), 281 (10).

IR (KBr): v/cm$^{-1}$=3355, 3234, 1683, 1595, 1517.

EXAMPLE 2

Synthesis of 6-Amino-11,12-dihydro-11-(2',3',4'-trimethoxyphenyl)benzo[c]-phenanthridine Hydrochloride A solution of 80 mmol 2-methylbenzonitrile (9.36 g) and 40 mmol 2,3,4-tri-methoxybenzaldehyde (7.85 g), in 40 ml DMPU was added dropwise to a stirred solution of 88 mmol potassium-tert-butylate (9.86 g) in 90 ml DMPU at 30° C. under an atmosphere of nitrogen. The resulting mixture was stirred for 3–4 h at 35–40° C. and then decomposed with 400 ml ice water containing 80 mmol ammonium chloride (8.8 g). The aqueous layer was extracted three times with 200 ml methylene chloride. After evaporation of the solvent, 20 ml 5N hydrochloric acid was added under vigorous stirring to obtain 6-amino-11,12-dihydro-11-(2',3',4'-trimethoxyphenyl)benzo[c]phenanthridine hydrochoride. The colourless precipitate was collected, washed with methylene chloride, recrystallized from methanol/water (3:1) and dried in an oil pump vacuum for 24 h.

Yield: 11,40 g (64% of theory), colourless crystals
melting point: 283° C.

| $C_{26}H_{25}N_2O_3Cl$ (448.95) | Calc.: | C 69.56 | H 5.61 | N 6.24 |
| | | O 10.69 | Cl 7.90 | |
| | Found: | C 69.51 | H 5.48 | N 6.21 |

$^1$H-NMR (DMSO-d$_6$, 300 MHz): δ/ppm (TMS)=3.08 (d, 1H, H-12a, $^2J_{(H-12a,H-12b)}$=15.8 Hz), 3.52 (mc, 1H, H-12b), 3.59 (s, 3H, —OCH$_3$), 3.79 (s, 3H, —OCH$_3$), 4.13 (s, 3H, —OCH$_3$), 5.04 (d, 1H, H-11, $^3J_{(H-11,H-12b)}$=7.0 Hz), 6.04 (d, 1H, ArH), 6.31 (d, 1H, ArH), 7.23 (d, 1H, ArH), 7.35 (mc, 1H, ArH), 7.44 (mc, 1H, ArH), 7.73 (d, 2H, ArH), 7.93 (mc, 1H, ArH), 8.48 (d, 1H, ArH), 8.62 (d, 1H, ArH), 9.80 (br, s, 2H, —NH$_2$), 14.04 (br, s, 1H, ≡N$^+$ —H).

$^{13}$C-NMR (DMSO-d$_6$, 75 MHz): δ/ppm (TMS)=30.2 (C-11), 34.8 (C-12), 55.5 (—OCH$_3$), 60.3 (—OCH$_3$), 61.2 (—OCH$_3$), 107.1, 123.4, 123.8, 125.8, 126.2, 127.1, 128.1, 129.2, 130.1, 135.0 (10C, C-1, -2, -3, -4, -7, -8, -9, -10, -5', -6'), 117.4, 117.5, 121.8, 127.4, 133.0, 135.2, 135.7, 141.7, 150.3, 152.3, 155.3 (11C, C-4a, -4b, -6, -6a, -10a, -10b, -12a, -1', -2', -3', -4').

IR (KBr): v/cm$^{-1}$=3258, 3072, 2934, 2834, 1642, 1620, 1600, 1570, 1554.

Release of the Base:

A solution of 6-Amino-11,12-dihydro-11-(2',3',4'-trimethoxy-phenyl)benzo[c]phenanthridine hydrochloride in 20 ml conc. ammonia and 250 ml diethyl ether was stirred vigorously for 1 h. The organic layer was separated and poured into 350 ml petroleum ether (50–70). The precipitate was collected. After evoporation of the solvent, further precipitate was collected and washed three times with a small amount of petroleum ether. The colourless crystals of 6-Amino-11,12-dihydro-11-(2',3',4'-trimethoxyphenyl)benzo[c]phenanthridine were dried in an oil pump vacuum for 24 h. melting point: 137° C.

| $C_{26}H_{24}N_2O_3$ (412.49) | Calc.: | C 75.71 | H 5.86 | N 6.79 |
|---|---|---|---|---|
| | | O 11.64 | | |
| | Found: | C 75.65 | H 5.88 | N 6.65 |

$^1$H-NMR (DMSO-d$_6$, 300 MHz): δ/ppm (TMS)=3.04 (d, 1H, H-12a, $^2J_{(H-12a,H-12b)}$=15.5 Hz), 3.57 (mc, 1H, H-12b), 3.63 (s, 3H, —OCH$_3$), 3.89 (s, 3H, —OCH$_3$), 4.18 (s, 3H, —OCH$_3$), 5.15 (d, 1H, H-11, $^3J_{(H-11,H-12b)}$=7.3 Hz), 5.20 (br, s, 2H, —NH$_2$), 6.12 (mc, 2H, ArH), 7.04 (d, 1H, ArH), 7.19 (mc, 1H, ArH), 7.31–7.41 (m, 2H, ArH), 7.54 (mc, 1H, ArH), 7.80 (mc, 2H, ArH), 8.36 (d, 1H, ArH).

$^{13}$C-NMR (DMSO-d$_6$, 75 MHz): δ/ppm (TMS)=31.3 (C-11), 39.9 (C-12), 55.6 (—OCH$_3$), 60.7 (—OCH$_3$), 61.3 (—OCH$_3$), 106.8, 122.9, 123.1, 123.7, 124.5, 125.4, 126.8, 128.2, 130.4 (10C, C-1, -2, -3, -4, -7, -8, -9, -10, -5', -6'), 118.5, 119.3, 129.3, 135.7, 135.9, 136.9, 142.5, 144.9, 151.2, 152.7, 156.0 (11C, C-4a, -4b, -6, -6a, -10a, -10b, -12, -1',-2', -3', -4').

MS (EI): m/z (%) 412 (M$^+$, 95), 397 (M$^+$ —CH$_3$, 10), 381 (M$^+$ —OCH$_3$, 37), 245 (M$^+$-2,3,4-Trimethoxyphenyl, 100), 231 (59), 201 (10), 168 (5), 153 (7).

IR (KBr): v/cm$^{-1}$=3426, 3310, 3178, 2918, 2815, 1630, 1595, 1557.

EXAMPLE 3

Synthesis of 6-Amino-11,12-dihydro-11-(3',4',5'-trimethoxyphenyl)benzo[c]-phenanthridine Hydrochloride A solution of 80 mmol 2-methylbenzonitrile (9.36 g) and 40 mmol 3,4,5-tri-methoxybenzaldehyde (7.85 g) in 40 ml DMPU was added dropwise to a stirred solution of 88 mmol potassium-tert-butylate (9.86 g) in 90 ml DMPU at 30° C. under an atmosphere of nitrogen. The resulting mixture was stirred for 3–4 h at 35–40° C. and then decomposed with 400 ml ice water containing 80 mmol ammonium chloride (8.8 g). The aqueous layer was extracted two times with 250 ml methylene chloride. After evaporation of the solvent, 10 ml conc. hydrochloric acid was added under vigorous stirring to obtain 6-amino-11,12-dihydro-11-(3',4',5'-trimethoxyphenyl)benzo[c]phenanthridine hydrochoride. The pale precipitate was collected, washed with methylene chloride, recrystallized from methanol/water (3:1) and dried in an oil pump vacuum for 24 h.

Yield: 10.7 g (60% of theory), colourless crystals melting point: 272° C.

| $C_{26}H_{25}N_2O_3Cl$ (448.95) | Calc.: | C 69.56 | H 5.61 | N 6.24 |
|---|---|---|---|---|
| | | O 10.69 | Cl 7.90 | |
| | Found: | C 69.48 | H 5.53 | N 6.17 |

$^1$H-NMR (DSMO-d$_6$, 300 MHz): δ/ppm (TMS)=3.13 (d, 1H, H-12a, $^2J_{(H-12a,H-12b)}$=15.7 Hz), 3.50 (s, 6H, 2 —OCH$_3$), 3.5* (mc, 1H, 1H-12b), 3.52 (s, 3H, —OCH$_3$), 4.83 (d, 1H, H-11, $^3J_{H-11,H-12b}$=6.5 Hz), 6.34 (s, 1H, ArH), 7.27 (d, 1H, ArH), 7.38 (mc, 1H, ArH), 7.45 (mc, 1H, ArH), 7.75 (mc, 1H, ArH), 7.98 (mc, 1H, ArH), 8.04 (d, 1H, ArH), 8.34 (d, 1H, ArH), 8.62 (d, 1H, ArH), 9.55 (br, s, 2H, —NH$_2$), 13.87 (br, s, 1H, ≡N$^+$ —H).

*overlapped by the signals of the methoxy groups $^{13}$C-NMR (DMSO-d$_6$, 75 MHz): δ/ppm (TMS)=35.9 (C-12), 36.7 (C-11), 55.6 (2C, 2 —OCH$_3$), 59.8 (—OCH$_3$), 104.6 (2C), 123.4, 124.5, 126.1, 127.1, 128.0, 129.2, 130.1, 135.1 (10C, C-1, -2, -3, -4, -7, -8, -9, -10, -2', -6'), 117.5, 117.9, 127.6, 132.7, 135.2, 135.9, 136.2, 137.1, 152.6 (2C), 155.3 (11C, C-4a, -4b, -6, -6a, -10a, -10b, -12a, -1', -3', -4', -5').

IR (KBr): v/cm$^{-1}$=3388, 31.56, 2940, 2842, 1665, 1633, 1598.

Release of the Base:

A solution of 6-Amino-11,12-dihydro-11-3',4',5'-trimethoxyphenyl)benzo[c]-phenanthridine hydrochloride in 10 ml conc. ammonia and 100 ml diethyl ether was stirred vigorously for 1 h. The organic layer was separated and poured into 150 ml petroleum ether (50–70). The precipitate was collected. After evoporation of the solvent, further precipitate was collected and washed two times with a small amount of petroleum ether. The colourless crystals of 6-Amino-11,12-dihydro-11-(3',4',5'-trimethoxyphenyl)-benzo[c]phenanihridine were dried in an oil pump vacuum for 24 h.

melting point: 182° C.

| $C_{26}H_{24}N_2O_3$ (412.49) | Calc.: | C 75.71 | H 5.86 | N 6.79 |
|---|---|---|---|---|
| | | O 11.64 | | |
| | Found: | C 75.70 | H 5.81 | N 6.68 |

$^1$H-NMR (DMSO-d$_6$, 300 MHZ): δ/ppm (TMS)=3.07 (d, 1H, H-12a, $^2J_{(H-12a,H-12b)}$=15.7 Hz), 3.54* (mc, 1H, H-12b), 3.55 (s, 6H, 2 —OCH$_3$), 3.70 (s, 3H, —OCH$_3$), 4.66 (d, 1H, H-11, $^3J_{(H-11,H-12b)}$=6.7 Hz), 4.74 (br, s, 2H, —NH$_2$), 6.25 (s, 2H, ArH), 7.05 (d, 1H, ArH), 7.19 (mc, 1H, ArH), 7.30–7.40 (m, 2H, ArH), 7.55 (mc, 1H, ArH), 7.82 (mc, 2H, ArH), 8.33 (d, 1H, ArH).

*overlapped by the signals of the methoxy groups $^{13}$C-NMR (DMSO-d$_6$, 75 MHz): δ/ppm (TMS)=37.8 (C-12), 39.9 (C-11), 56.5 (2C, 2 —OCH$_3$), 61.3 (—OCH$_3$), 105.3 (2C), 123.8, 124.3, 125.1, 126.1, 127.6, 128.9, 129.1, 131.0 (10C, C-1, -2, -3, -4, -7, -8, -9, -10, -2', -6'), 118.4, 118.9, 135.5, 136.0 (2C), 137.0, 139.7, 144.7, 153.5 (2C), 156.1 (11C, C-4a, -4b, -6, -6a, -10a, -10b, -12a, -1', -3', -4', -5').

MS(EI): m/z (%)=412 (M$^+$, 50), 397 (M$^+$ —CH$_3$, 8), 245 (M$^+$-3,4,5-trimethoxyphenyl, 68), 206 (9), 201 (6), 168 (3), 153 (11), 77 (8), 43 (100).

IR (KBr): v/cm$^{-1}$=3495, 3382, 2943, 2848, 1632, 1592, 1508.

Pharmacological Test Results of the Compounds of Examples 1 to 3

In order to examine the pharmacological properties, these compounds (BP-7, BP-8, BP-D8) as well as 6-Amino-11-(2',4'-dimethoxyphenyl)benzo[c]-phenanthridine perchlorate (BP-D3) [PCT/WO 97/14683] were examined in an "in vivo-hollow fiber assay" of the National Cancer Institute (NCI), Bethesda, Md., USA.

Compounds were tested against a panel of 12 human pathogenic tumour cell lines of six types of cancer (non-small cell lung cancer, melanoma, breast cancer, ovarian cancer, colon cancer, CNS cancer).

The cell lines were cultivated in polyvinylidenfluorine hollow fibers which are permeable to small molecules and which were implanted into nude mice. Three hollow fibers were implanted every animal intraperitoneally and subcutaneously which means three tumor cell lines could be examined in each animal in two physiological sites.

The animals were treated four times with a dose of the test substance with a time interval of 24 hours. For this purpose, every compound was administered at two concentrations. At the end of the treatment the hollow fibers were regained and the number of the vital tumour cells or rather of the protein biomass was determined photometrically by an MTT-Formazan-Assay in order to determine the inhibition of growth by the phenanthridines. Mice with prepared tumour cell cultures in hollow fibers which were only treated by solvent served as control.

The evaluation of test results is based on a point system given by NCI.

Each administration of a test substance which leads to a reduction of the tumour cell growth of at least 50% is given a score of two points. The maximum number of points for one compound is therefore 96 points (12 cell lines*2 implantation sites*2 concentrations of the test substance*2 points). In addition for further specification the results on subcutaneously and intraperitoneally implanted hollow fibers are treated separately. There are three criteria given by NCI. A test substance in the "in vivo-hollow fiber assay" has to fulfill at least one criterion in order to be regarded as suitable for further tests:

(a) the total sum of the points from intraperitoneal and subcutaneous application must be higher than 20.
(b) The total sum of the points of the subcutaneous application must be higher than 8.
(c) After the treatment the vital tumour cell mass of at least one cell line must be less than the starting value (cell kill characteristics).

Out of all tested phenanthridines the 6-Amino-11-(3',4',5'-trimethoxyphenyl)benzo[c]phenanthridine perchlorate (BP-D7) showed the highest activity in the "in vivo-hollow fiber assay" and fulfilled the criteria a, b and c (see tab. 1).

TABLE 1

Results of the phenanthridines in the in vivo-hollow-fiber assay of the National Cancer Institute

| Compound | Points (sum) | Points (intra-peritoneal) | Points (subcutaneous) | Cell killing properties |
|---|---|---|---|---|
| BP-D7 | 28 | 14 | 14 | Yes |
| BP-8 | 20 | 10 | 10 | Yes |
| BP-7 | 16 | 6 | 10 | Yes |
| BP-D3 | 10 | 2 | 8 | Yes |

BP-D7 6-Amino-11-(3',4',5'-trimethoxyphenyl)benzo[c]phenanthridine perchlorate
BP-8 6-Amino-11,12dihydro-11-(2',3',4'-trimethoxyphenyl)benzo[c]-phenanthridine hydrochloride
BP-7 6-Amino-11,12dihydro-11-(3',4',5'-trimethoxyphenyl)benzo[c]-phenanthridine hydrochloride
BP-D3 6-Amino-11-(2',4'-dimethoxyphenyl)benzo[c]phenanthridine perchlorate 6-Amino-11,12dihydro-11-(2',3',4'-trimethoxyphenyl)benzo[c]-phenanthridine hydrochloride (BP-8) and 6-Amino-11,12-dihydro-11(3',4',5'-tri-methoxy-phenyl)benzo[c]phenanthridine hydrochloride (BP-7) fulfill the criteria (b) and (c), on the other hand, 6-Amino-11-(2',4'-dimethoxy-phenyl)benzo[c]-phenanthridine perchlorate (BP-D3) fulfills the criteria(c) only. Thus the phenanthridines BP-D7, BP-8, and BP-7 achieve higher points than the compound BP-D3 in all separate categories (subcutaneous and intraperitoneal) as well as in the total sum of all points.

The FIG. 1 shows the test results for these phenanthridines in a form of a bar chart.

I claim:

1. A phenanthridine derivative of the formula I

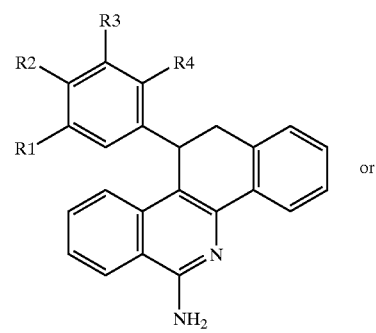

or

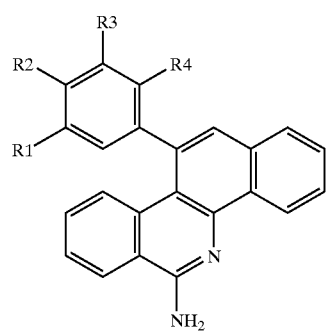

II wherein three of $R_1$ to $R_4$ are methoxy and one is hydrogen; or an ionic form thereof, or a pharmaceutically acceptable salt thereof.

2. The phenanthridine derivative according to claim 1 having the formula

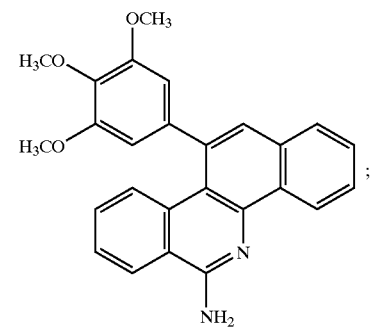

;

or an ionic form thereof, or a pharmaceutically acceptable salt thereof.

3. The phenanthridine derivative according to claim 1 having the formula

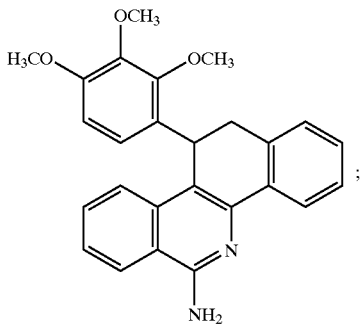

or an ionic form thereof, or a pharmaceutically acceptable salt thereof.

4. The phenanthridine derivative according to claim 1 having the formula

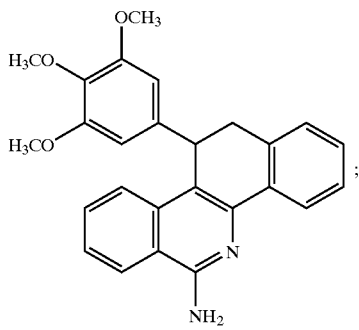

or an ionic form thereof, or a pharmaceutically acceptable salt thereof.

5. A pharmaceutical composition for antitumoural therapy and tumor prophylaxis which comprises an effective amount of at least one phenanthridine derivative according to claim 1; and at least one pharmaceutically acceptable carrier and/or dilution medium.

6. The pharmaceutical composition according to claim 5 wherein at least one phenanthridine derivative is

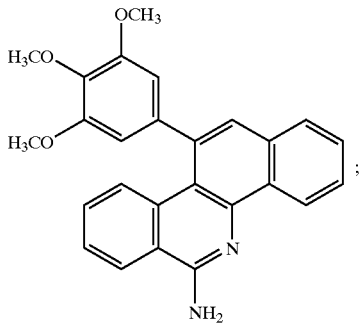

or an ionic form thereof, or a pharmaceutically acceptable salt thereof.

7. The pharmaceutical composition according to claim 5 wherein at least one phenanthridine derivative is

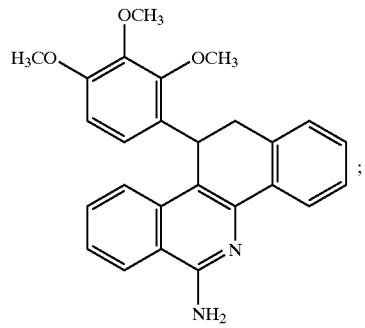

or an ionic form thereof, or a pharmaceutically acceptable salt thereof.

8. The pharmaceutical composition according to claim 5 wherein at least one phenanthridine derivative is

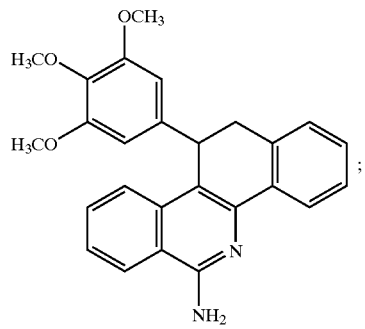

or an ionic form thereof, or a pharmaceutically acceptable salt thereof.

9. The pharmaceutical composition according to claim 5, where the pharmaceutical composition is an oral composition.

10. The pharmaceutical composition according to claim 5, where the pharmaceutical composition is a topical composition.

11. A method of treating a tumor or of tumor prophylaxis which comprises administering an effective amount of at least one phenanthridine derivative according to claim 1 to a mammal in need thereof.

12. The method according to claim 11, wherein at least one phenanthridine derivative is

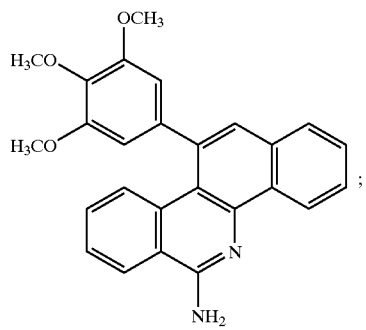

or an ionic form thereof, or a pharmaceutically acceptable salt thereof.

13. The method according to claim 11, wherein at least one phenanthridine derivative is

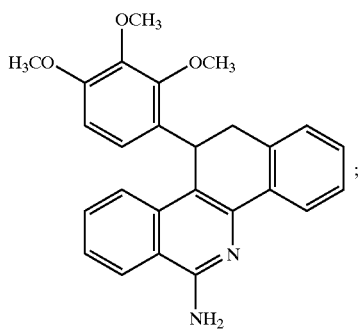

or an ionic form thereof, or a pharmaceutically acceptable salt thereof.

14. The method according to claim 11, wherein at least one phenanthridine derivative is

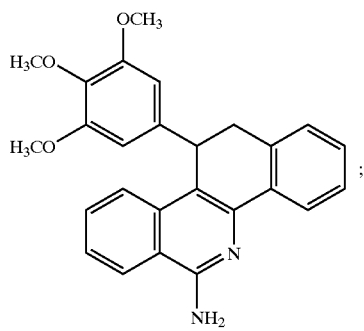

or an ionic form thereof, or a pharmaceutically acceptable salt thereof.

15. The method according to claim 11, which comprises orally administering.

16. The method according to claim 11, which comprises topically administering.

* * * * *